United States Patent [19]

Yamamoto et al.

[11] 4,155,938
[45] May 22, 1979

[54] OXIDATION OF OLEFINS

[75] Inventors: Haruhisa Yamamoto; Novuaki Yoneyama; Shinichi Akiyama, all of Takaoka, Japan

[73] Assignee: Nippon Zeon Co., Ltd., Japan

[21] Appl. No.: 831,672

[22] Filed: Sep. 8, 1977

[30] Foreign Application Priority Data

Dec. 13, 1976 [JP] Japan ................... 51-149596

[51] Int. Cl.$^2$ ............................................. C07C 47/22
[52] U.S. Cl. ................................ 260/604 R; 252/432; 252/462; 252/468
[58] Field of Search ............... 260/604 R; 252/435, 252/432, 437, 462, 464, 468, 469, 470

[56] References Cited

U.S. PATENT DOCUMENTS

| | | | |
|---|---|---|---|
| 3,725,482 | 4/1973 | Cant et al. | 260/604 R |
| 3,778,386 | 12/1973 | Takenaka et al. | 252/432 |
| 3,885,020 | 5/1975 | Whelan | 423/245 |
| 3,928,462 | 12/1975 | Shiraishi et al. | 260/604 R |
| 3,968,166 | 7/1976 | Shiraishi etal. | 260/604 R |
| 3,989,674 | 11/1976 | Sinfelt et al. | 260/604 R |

Primary Examiner—Werren B. Lone
Attorney, Agent, or Firm—Wenderoth, Lind & Ponack

[57] ABSTRACT

A catalyst for oxidation of olefins which has a composition of the general formula

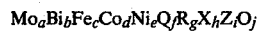

$$Mo_aBi_bFe_cCo_dNi_eQ_fR_gX_hZ_iO_j$$

wherein Q is at least one element selected from Au and Nd; R is at least one element selected from K, Rb, Cs and Tl; X is at least one element selected from P, As and B; Z is at least one element selected from Ce, Ti, Te, Zn, Ge, Sn, Cr, Ga, La, In, Al, Cd, Pd, Mn, V, W, Pb, Nb, Ag, Zr, Cu and U; a, b, c, d, e, f, g, h and i respectively represent the numbers of Mo, Bi, Fe, Co, Ni, Q, R, X and Z atoms, and when a is 12, b is 0.1–10, c is 0.5–40, d is 0–12, e is 0–12 with the proviso that the sum of d and e is 0.5–15, f is 0.1–8, g is 0.01–5, h is 0–5, i is 0–12; and j is the number of oxygen atoms which satisfies the atomic valences of the other elements.

12 Claims, No Drawings

OXIDATION OF OLEFINS

This invention relates to a catalyst for oxidation of olefins, and a process for producing unsaturated aldehydes by oxidizing olefins in the presence of the aforesaid catalyst.

Some of the terms used in the present application are defined as follows:

The "olefins" denote olefins containing 3 carbon atoms in the straight chain, such as propylene, isobutylene and isoamylene.

The "first-stage oxidation" denotes the catalytic vapor-phase reaction of olefins with molecular oxygen at high temperatures in the presence of a catalyst to form the corresponding unsaturated aldehydes.

The "second-stage oxidation" denotes the catalytic vapor-phase reaction of the unsaturated aldehydes with molecular oxygen at high temperatures in the presence of a catalyst to form the corresponding unsaturated carboxylic acids.

The "continuous first stage-second stage method" denotes a method for producing unsaturated carboxylic acids from olefins by feeding the gaseous reaction mixture formed in the first-stage oxidation directly to a second-stage oxidation zone to perform the second-stage oxidation.

The "catalyst for oxidation of olefins", or the "catalyst for the first-stage oxidation" denotes a catalyst which is used in the first-stage oxidation.

The "catalyst for the second-stage oxidation" denotes a catalyst which is used in the second-stage oxidation.

It is known to produce unsaturated aldehydes such as acrolein and methacrolein by oxidizing the corresponding olefins such as propylene and isobutylene, and to produce unsaturated carboxylic acids such as acrylic acid and methacrylic acid by oxidizing the corresponding unsaturated aldehydes. Known prior techniques for the production of unsaturated carboxylic acids from the corresponding olefins include a method which comprises separating an unsaturated aldehyde from the reaction mixture obtained by the first-stage oxidation, and after purifying it, submitting it to a second-stage oxidation, and a method which involves performing the first-stage oxidation and the second stage oxidation successively without working up the first-stage reaction mixture (British Pat. No. 939,713). The latter is considered to be commercially advantageous because it does not require a treating step such as the separation and purification of the unsaturated aldehyde, and therefore has advantages in apparatus, operation and economy.

However, the continuous first stage-second stage method generally gives far inferior results to the case of independently performing the second-stage oxidation using the purified unsaturated aldehyde as a starting material. This tendency is especially outstanding in the production of methacrylic acid from isobutylene. For this reason, no suggestion has been made so far which would make possible the commercial production of methacrylic acid by the continuous first stage-second stage method.

The underlying difficulties are believed to be the formation of by-product impurities and the remaining of unreacted isobutylene in the first-stage oxidation. The present inventors carefully studied these difficulties, and found that the reaction mixture obtained by the first-stage oxidation contains unsaturated hydrocarbons such as diisobutylene, benzene, toluene, xylene and ethylbenzene in addition to the unreacted isobutylene and a tar-like by-product, and the presence of these hydrocarbons is a main cause for the inferior reaction results in the second-stage oxidation.

In the production of methacrylic acid from isobutylene by the continuous first stage-second stage method, it is desired to develop a novel oxidation catalyst that simultaneously meets the following two requirements which seem to be inconsistent with each other.

(1) It should afford a high conversion of isobutylene and thus reduce the amount of the unreacted isobutylene.

(2) It should reduce the formation of not only a tar-like by-product but also unsaturated hydrocarbons such as diisobutylene, benzene, toluene, xylene and ethylbenzene.

In addition to these requirements, such a catalyst should also meet normal requirements for industrial catalysts such as a high selectivity to MAL (which is associated with a high one-pass yield), and a long active lifetime.

Accordingly, it is an object of this invention to provide a novel catalyst for oxidation of olefins, which can afford unsaturated aldehydes from olefins in a high selectivity and a high one-pass yield, and has a long active lifetime.

Another object of this invention is to provide a novel catalyst for oxidation of olefins which meets the two requirements described above.

Still another object of this invention is to provide a process for preparing unsaturated aldehydes in a high selectivity and a high yield by using such a catalyst for oxidation of olefins.

According to this invention, there is provided a catalyst which can achieve these objects, said catalyst having the composition $$Mo_aBi_bFe_cCo_dNi_eQ_fR_gX_hZ_iO_j$$

wherein Q is at least one element selected from Au and Nd; R is at least one element selected from K, Rb, Cs and Tl; X is at least one element selected from P, As and B; Z is at least one element selected from Ce, Ti, Te, Zn, Ge, Sn, Cr, Ga, La, In, Al, Cd, Pd, Mn, V, W, Pb, Nb, Ag, Zr, Cu and U; a, b, c, d, e, f, g, h, and i respectively represent the numbers of Mo, Bi, Fe, Co, Ni, Q, R, X and Z atoms, and when a is 12, b is 0.1–10, c is 0.5–40, d is 0–12, e is 0–12 with the proviso that the sum of d and e is 0.5–15, f is 0.1–8, g is 0.01–5, h is 0–5, and i is 0–12; and j is the number of oxygen atoms which satisfies the atomic valences of the other elements.

A catalyst of the above general formula in which when a is 12, b is 0.5–7, c is 1–35, d is 0–10, e is 0–10 with the proviso that the sum of d and e is 0.5–12, f is 0.1–6, g is 0.01–4, h is 0–4, and i is 0–8 is a preferred embodiment of the present invention.

A catalyst of the above general formula wherein when a is 12, b is 0.5–7, c is 8–30, d is 0–10, e is 0–10 with the proviso that the sum of d and e is 0.5–12, f is 0.1–4, g is 0.01–3, h is 0–3, and i is 0–8 is an especially preferred embodiment of the invention.

Although the exact structure of the catalyst of this invention is not clear, the composition of the ingredients forming the catalyst is believed to be basically expressed by the above general formula.

The use of these catalysts of the invention can afford methacrolein in a high yield and a high selectivity even when the conversion of isobutylene in its oxidation is high, and can drastically reduce the amounts of by-product unsaturated hydrocarbons such as diisobutylene, benzene, toluene, xylene or ethylbenzene. Accordingly, the catalysts of this invention are very suitable for production of methacrolein, and when used as a first-stage oxidation catalyst in the continuous first stage-second stage method, they do not substantially hamper the second-stage oxidation reaction over long periods of time. Furthermore, the catalysts of this invention can give acrolein in a high yield in the catalytic oxidation of propylene, and are very effective in the continuous first stage-second stage method for producing acrylic acid from propylene.

Such an effect of this invention can be specifically obtained by the inclusion of Au or Nd in the catalyst ingredients as shown in the above general formula. If these ingredients are not present, the activities of the catalysts are low, and the formation of by-product unsaturated hydrocarbons greatly increases.

Known catalysts having a composition similar to that of the catalysts of this invention show good performance only when the number of Fe atoms is within a very narrow range of 0.5 to 3 with the number of Mo atoms taken as 12 (for example, Japanese Patent Publication No. 17253/73). In contrast, the catalysts of this invention exhibit a high activity when the number of Fe atoms is within a broad range of 0.5 to 40, and exhibit the best performance when the number of Fe atoms is within the range of 8 to 30.

The catalysts of this invention can be prepared by various methods known in the art such as an evaporation method, an oxide mixing method and a coprecipitation method. The starting materials for the individual elements in the catalyst may be not only their oxides, but any other compounds which will constitute the catalyst of this invention by calcination. Examples of these starting materials are salts containing these elements (such as ammonium salts, nitrate salts, carbonate salts, organic acid salts, and halides), free acids, acid anhydrides, condensed acids, and heteropolyacids containing molybdenum such as phosphomolybdic acid or silicomolybdic acid, and their salts such as ammonium salts or metal salts. The use of a silicon-containing compound such as silicomolybdic acid does not adversely affect the activity of the resulting catalyst.

Calcination treatment for the purpose of catalyst preparation, catalyst activation, etc. is performed usually at 300° to 900° C., preferably 450° to 700° C. for about 4 to 16 hours. If desired, a primary calcination treatment may be performed at a temperature below the above-mentioned calcination temperature before the above calcination treatment.

The catalysts of this invention can be used directly as prepared, and also as deposited on a carrier of a suitable shape, or as diluted with a carrier (diluent) in the form of powder, sol, gel, etc. Known carriers can be used for this purpose. Examples include titanium dioxide, silica gel, silica sol, diatomaceous earth, silicon carbide, alumina, pumice, silica-alumina, bentonite, zirconia, zeolite, and refractories. Silicon-containing carriers are especially suitable.

The amount of the carrier can be suitably chosen. The catalyst is made into a suitable shape such as powder or tablets, and can be used in any of a fixed bed, a moving bed, and a fluidized bed.

The catalysts of this invention are useful for oxidizing olefins having three carbon atoms in the straight chain, such as propylene, isobutylene and isoamylene, especially isobutylene. These olefins need not to be highly pure, but may contain impurities. However, when the oxidation is performed by the continuous first stage-second stage method, the inclusion of large amounts of impurities possibly containing unsaturated hydrocarbons in the reacted gas from the first-stage oxidation is undesirable. Molecular oxygen may be singly used, but for commercial operations, the use of air is practical. Furthermore, in this reaction, the molecular oxygen may be diluted with an inert gas which does not adversely affect the reaction, such as steam, nitrogen, argon or carbon dioxide gas. It is especially preferred to dilute it with steam.

In the production of unsaturated aldehydes from the corresponding olefins using the catalysts of this invention, the reaction temperature is 250° to 700° C., preferably 250° to 550° C.; the reaction pressure is normal atmospheric pressure to 10 atmospheres; the space velocity (SV) of the entire starting gases is 200 to 10000 $hr^{-1}$, preferably 300 to 6000 $hr^{-1}$ (based on STP); the olefin concentration in the fed starting gases is 0.5 to 25% by volume; and the olefin to oxygen ratio is 1:0.5–7. The preferred composition of the starting gaseous mixture is olefin:air:steam=1:3–30:5–90 (molar ratio).

The reaction conditions in the first-stage oxidation in the continuous first stage-second stage method can be easily determined experimentally if a catalyst for the second-stage oxidation is set. Hence, the reaction conditions for the first-stage oxidation cannot be definitely fixed. Usually, however, the reaction temperature is 250° to 700° C., preferably 250° to 550° C.; the reaction pressure is normal atmospheric pressure to 10 atmospheres; the space velocity of the entire starting gases is 200 to 10000 $hr^{-1}$, preferably 300 to 4000 $hr^{-1}$; the olefin concentration is 0.5 to 10% by volume, preferably 0.5 to 8% by volume; the olefin to oxygen ratio is 1:1.5–7; and the preferred composition of the gaseous mixture is olefin:air:steam=1:7.5–30:5–90 (molar ratio).

For the second-stage oxidation in the continuous first stage-second stage method, any known catalysts can be used. Examples include P—Mo—R (R is at least one of Tl, alkali metals and alkaline earth metals) type oxidation catalysts; oxidation catalysts having compositions resulting from incorporating the above P—Mo—R type oxidation catalysts with at least one element selected from Si, Cr, Al, Ge, Ti, V, W, Bi, Nb, B, Ga, Pb, Sn, Co, Pd, As, Zr, Sb, Te, Fe, Ni, In, Cu, Ag, Mn, La, Nb, Ta and Sm; P—Mo—As type oxidation catalysts; P—Mo—As—alkali metal type oxidation catalysts; oxidation catalysts having compositions resulting from the incorporation of the P—Mo—As—alkali metal type catalysts with at least one element selected from V, W, Cu, Fe, Mn and Sn; P—Mo—Sb type oxidation catalysts; oxidation catalysts having compositions resulting from the incorporation of the P—Mo—Sb type catalysts with at least one element selected from W, Fe, Co, V, Al, Pb, Cr, Sn, Bi, Cu, Ni, Mg, Ca, Ba and Zn; P—Mo—Pd type oxidation catalysts; P—Pd—Sb type oxidation catalysts; oxidation catalysts having compositions resulting from the incorporation of the P—Pd—Sb type catalysts with at least one element selected from Bi, Pb, Cr, Fe, Ni, Co, Mn, Sn, U and Ba; and oxidation catalysts having compositions resulting from the incorporation of the aforementioned oxidation catalysts with ammonium.

The second-stage oxidation is performed under substantially the same reaction conditions as in the first-stage oxidation, but as described above, specific conditions are selected according to the catalyst used. Preferably, the first-stage reaction mixture obtained under the aforesaid reaction conditions is directly offered as a starting material in the second-stage oxidation, and reacted under conditions suitable for the catalyst used.

The following examples specifically illustrate the present invention. In these examples, the conversion, selectivity and one-pass yield are calculated in accordance with the following equations. All analyses were made by gas chromatography. For simplicity, the indication of oxygen in the catalyst composition is omitted.

In the following description, i-B stands for isobutylene, MAL for methacrolein; and MAA for methacrylic acid. The reaction results obtained by using propylene instead of isobutylene can be calculated by substituting propylene for i-B, acrolein for MAL, and acrylic acid for MAS in the following equations.

[Calculating equations for the results of the first-stage oxidation]

$$\text{i-B conversion (\%)} = \frac{\text{Reaction i-B (moles)}}{\text{Fed i-B (moles)}} \times 100$$

$$\begin{aligned}\text{Percentage of unsaturated hydrocarbons} =& \left[\frac{\text{Unreacted i-B (moles)}}{\text{Fed i-B (moles)}}\right.\\ &+ \frac{\text{Formed diisobutylene (based on carbon)}}{\text{Fed i-B (based on carbon)}}\\ &+ \frac{\text{Formed benzene (based on carbon)}}{\text{Fed i-B (based on carbon)}}\\ &+ \frac{\text{Formed toluene (based on carbon)}}{\text{Fed i-B (based on carbon)}}\\ &+ \frac{\text{Formed xylene (based on carbon)}}{\text{Fed i-B (based on carbon)}}\\ &+ \left.\frac{\text{Formed ethylbenzene (based on carbon)}}{\text{fed i-B (based on carbon)}}\right.\end{aligned}$$

$$\text{One-pass yield of MAL (\%)} = \frac{\text{Formed MAL (moles)}}{\text{Fed i-B (moles)}} \times 100$$

$$\text{Selectivity of MAL (\%)} = \frac{\text{Formed MAL (moles)}}{\text{Reaction i-B (moles)}} \times 100$$

[Calculating equations for the results of the second-stage oxidation]

$$\text{MAL conversion (\%)} = \frac{\text{Reaction MAL (moles)}}{\text{Fed MAL (moles)}} \times 100$$

$$\text{One-pass yield of MAA (based on MAL) (\%)} = \frac{\text{Formed MAA (moles)}}{\text{Fed MAL (moles)}} \times 100$$

$$\text{Selectivity of MAA (based on MAL) (\%)} = \frac{\text{Formed MAA (moles)}}{\text{Reacted MAL (moles)}} \times 100$$

$$\text{Conversion of unsaturated hydrocarbons (\%)} = \frac{\text{Reacted unsaturated hydrocarbons (based on carbon)}}{\text{Fed unsaturated hydrocarbons (based on carbon)}} \times 100$$

$$\text{One-pass yield of MAA (based on i-B) (\%)} = \frac{\text{Formed MAA (moles)}}{\text{i-B) fed to the first-stage oxidation zone (moles)}} \times 100$$

EXAMPLES 1 TO 5

Bismuth nitrate (48.5 g), 116.5 g of cobalt nitrate, 29.1 g of nickel nitrate, 484.8 g of ferric nitrate and 10.1 g of potassium nitrate were added to 150 ml of water and dissolved by heating to form a solution (solution A). Separately, 212 g of ammonium molybdate was dissolved in 400 ml of water by heating, and 5.76 g of 85% phosphoric acid was added to form a solution (solution B). Furthermore, 41.2 g of tetrachloroauric acid (III) was dissolved in 200 ml of water by heating to form a solution (solution C).

Solution B was mixed with solution A which was stirred at an elevated temperature. After thorough mixing, solution C was added. With thorough stirring, the mixture was evaporated to dryness, and then dried at 120° C. for 8 hours. The dried product was calcined at 600° C. for 16 hours in a muffle furnace. The solid obtained was pulverized to form particles having a size of 4 to 8 mesh.

The composition of the catalyst of the invention so prepared was $Mo_{12}Bi_1Fe_{12}Co_4Ni_1Au_1P_{0.5}K_1$.

By the same procedure as above, various catalysts having different compositions as shown in Table 1 were prepared.

Using these catalysts as first-stage oxidation catalysts, a continuous first stage-second stage reaction was performed by the following procedure.

(1) First-stage oxidation reaction 100 ml of the catalyst obtained was filled into a stainless steel reaction tube having an inside diameter of 2.5 cm and a length of 60 cm, and heated over a metal bath. A starting gaseous mixture of isobutylene, air and steam in a mole ratio of 4:55:41 was passed through the catalyst layer at a space velocity of 2000 hr$^{-1}$.

(2) Second-stage oxidation reaction

As a catalyst for the second-stage oxidation, 100 ml of the Mo—P—Cs—Cr catalyst disclosed in Example 1 of the specification of Japanese Patent Publication No. 10846/75 [Mo:P:Cs:Cr=1:0.16:0.16:0.16 (atomic ratio); calcined at 450° C.; catalyst particle diameter 4–8 mesh] was filled into a stainless steel reaction tube having an inside diameter of 2.5 cm and a length of 60 cm, and heated over a metal bath. The reacted gas obtained by the first-stage oxidation was directly passed through the catalyst layer.

The results obtained in the first-stage oxidation and the second-stage oxidation are shown in Table 1. In Table 1, the reaction temperatures refer to those of the metal bath which were maintained constant (the same will apply hereinbelow).

Table I

Results of the first-stage oxidation

| Example | Catalyst composition (atomic ratio) | | | | | | | Reaction temperature (°C.) | i-B conversion (%) | Proportion of unsaturated hydrocarbons formed (%) | MAL one-pass yield (%) | MAL Selectivity (%) |
|---|---|---|---|---|---|---|---|---|---|---|---|---|
| | Mo | Bi | Fe | Co | Ni | Au | P | K | | | | | |
| 1 | 12 | 1 | 12 | 4 | 1 | 1 | 0.5 | 1 | 340 | 96.8 | 3.9 | 76.5 | 79.0 |
| 2 | 12 | 1 | 4 | 4 | 1 | 1 | 0.5 | 1 | 365 | 96.5 | 4.5 | 74.7 | 77.4 |
| 3 | 12 | 1 | 30 | 4 | 1 | 1 | 0.5 | 1 | 378 | 97.1 | 3.7 | 76.3 | 78.6 |
| 4 | 12 | 1 | 12 | 4 | 1 | 2 | 0.5 | 1.5 | 360 | 97.3 | 3.8 | 77.9 | 80.1 |
| 5 | 12 | 1 | 12 | 4 | 1 | 0.5 | 1 | 0.5 | 342 | 97.2 | 3.6 | 76.4 | 78.6 |

Results of the second-stage oxidation

| | Reaction | MAA (based on MAL) | Conversion of | One-pass yield |

Table I-continued

| Example | temperature (°C.) | MAL conversion (%) | One-pass yield (%) | Selectivity (%) | unsaturated hydrocarbons (%) | of MAA (based on i-B) (%) |
|---|---|---|---|---|---|---|
| 1 | 335 | 76.2 | 57.2 | 75.1 | 100 | 43.8 |
| 2 | 335 | 75.8 | 56.3 | 74.3 | 100 | 42.1 |
| 3 | 335 | 77.1 | 58.3 | 75.6 | 100 | 44.5 |
| 4 | 335 | 76.4 | 57.2 | 74.9 | 100 | 44.6 |
| 5 | 335 | 76.5 | 57.7 | 75.4 | 100 | 44.1 |

EXAMPLES 6 TO 17

A catalyst having the composition $Mo_{12}Bi_1Fe_{12}Co_4Ni_1Nd_1P_{0.5}K_1$ was prepared in the same way as in Example 1 except that 43.8 g of neodymium nitrate was used instead of 41.2 g of tetrachloroauric acid (III). Various catalysts having different compositions as shown in Table 2 were prepared by the same procedure.

The performance of these catalysts were evaluated in the same way as in Example 1. The results are shown in Table 2.

Table 2

Results of the first-stage oxidation

| Example | Catalyst composition (atomic ratio) | | | | | | | | Reaction temperature (°C.) | i-B conversion (%) | Proportion of unsaturated hydrocarbons formed (%) | MAL One-pass yield (%) | MAL Selectivity (%) |
|---|---|---|---|---|---|---|---|---|---|---|---|---|---|
| | Mo | Bi | Fe | Co | Ni | Nd | P | K | | | | | |
| 6 | 12 | 1 | 12 | 4 | 1 | 1 | 0.5 | 1 | 340 | 96.7 | 3.9 | 76.3 | 78.9 |
| 7 | 12 | 1 | 6 | 4 | 1 | 1 | 0.5 | 1 | 370 | 96.5 | 4.2 | 75.4 | 78.1 |
| 8 | 12 | 1 | 18 | 4 | 1 | 1 | 0.5 | 1 | 360 | 97.0 | 3.7 | 78.1 | 80.5 |
| 9 | 12 | 1 | 30 | 4 | 1 | 1 | 0.5 | 1 | 375 | 96.5 | 4.0 | 77.3 | 80.1 |
| 10 | 12 | 1 | 4 | 4 | 1 | 1 | 0.5 | 1 | 365 | 96.3 | 4.1 | 75.1 | 78.0 |
| 11 | 12 | 3 | 12 | 4 | 1 | 1 | — | 0.75 | 344 | 97.2 | 3.7 | 78.2 | 80.5 |
| 12 | 12 | 6 | 12 | 4 | 1 | 0.5 | 0.5 | 0.75 | 345 | 96.8 | 3.8 | 76.8 | 79.3 |
| 13 | 12 | 3 | 12 | — | 5 | 3 | 0.5 | 0.75 | 330 | 98.2 | 2.8 | 77.2 | 78.6 |
| 14 | 12 | 1 | 12 | 4 | 1 | 0.2 | 0.5 | 1 | 350 | 96.4 | 4.0 | 77.8 | 80.7 |
| 15 | 12 | 1 | 12 | 4 | 1 | 6 | 2 | 2 | 338 | 98.0 | 3.9 | 78.5 | 80.1 |
| 16 | 12 | 1 | 12 | 5 | — | 2 | 0.5 | 1.5 | 330 | 98.5 | 2.6 | 79.8 | 81.0 |
| 17 | 12 | 1 | 12 | 4 | 1 | 0.7 | 0.5 | 0.5 | 345 | 97.1 | 3.7 | 76.7 | 79.0 |

Results of the second-stage oxidation

| Example | Reaction temperature (°C.) | MAL conversion (%) | MAA (based on MAL) One-pass yield (%) | MAA (based on MAL) Selectivity (%) | Conversion of unsaturated hydrocarbons (%) | One-pass yield of MAA (based on i-B) (%) |
|---|---|---|---|---|---|---|
| 6 | 335 | 76.1 | 57.1 | 75.0 | 100 | 43.6 |
| 7 | 335 | 75.6 | 56.9 | 75.3 | 100 | 42.9 |
| 8 | 335 | 76.9 | 58.3 | 75.8 | 100 | 45.5 |
| 9 | 335 | 76.3 | 57.2 | 75.0 | 100 | 44.2 |
| 10 | 335 | 75.3 | 57.3 | 76.1 | 100 | 43.0 |
| 11 | 335 | 76.4 | 58.4 | 76.4 | 100 | 45.7 |
| 12 | 335 | 76.0 | 58.0 | 76.3 | 100 | 44.5 |
| 13 | 335 | 80.5 | 61.8 | 76.8 | 100 | 47.7 |
| 14 | 335 | 75.9 | 56.8 | 74.8 | 100 | 44.2 |
| 15 | 335 | 77.0 | 57.5 | 74.7 | 100 | 45.1 |
| 16 | 335 | 78.8 | 59.9 | 76.0 | 100 | 47.8 |
| 17 | 335 | 76.7 | 57.9 | 75.5 | 100 | 44.4 |

EXAMPLES 18 to 31

Catalysts were prepared in the same way as in Examples 1 and 6 except that Ce, Ti, Zn, Cr, La, Al, Cd, Pb, W or Cu was further added to the catalysts prepared in Examples 1 and 6. Using these catalysts, the continuous first stage-second stage reaction as in Example 1 was performed. The results are shown in Table 3.

Table 3

Results of the first-stage oxidation

| Example | Catalyst composition (atomic ratio) | | | | | | | | | | Reaction temperature (°C.) | i-B conversion (%) | Proportion of unsaturated hydrocarbons formed (%) | MAL One-pass yield (%) | MAL Selectivity (%) |
|---|---|---|---|---|---|---|---|---|---|---|---|---|---|---|---|
| | Mo | Bi | Fe | Co | Ni | Au | Nd | P | K | Z | | | | | |
| 18 | 12 | 1 | 12 | 4 | 1 | 1 | — | 0.5 | 1 | 3 (Ti) | 340 | 98.1 | 3.0 | 78.4 | 79.9 |
| 19 | 12 | 1 | 12 | 4 | 1 | 1 | — | 0.5 | 1 | 1 (La) | 340 | 98.3 | 2.9 | 78.1 | 79.5 |
| 20 | 12 | 1 | 12 | 4 | 1 | 1 | — | 0.5 | 1 | 1 (Pd) | 340 | 97.4 | 3.3 | 78.5 | 80.6 |
| 21 | 12 | 1 | 12 | 4 | 1 | 1 | — | 0.5 | 1 | 1 (Cu) | 340 | 98.2 | 3.1 | 78.3 | 79.7 |
| 22 | 12 | 1 | 12 | 4 | 1 | — | 1 | 0.5 | 1 | 1 (Ce) | 340 | 97.1 | 3.4 | 76.8 | 79.1 |
| 23 | 12 | 1 | 12 | 4 | 1 | — | 1 | 0.5 | 1 | 3 (Ti) | 340 | 97.5 | 2.9 | 77.0 | 79.0 |
| 24 | 12 | 1 | 12 | 4 | 1 | — | 1 | 0.5 | 1 | 2 (Zn) | 340 | 97.0 | 3.6 | 77.1 | 79.5 |
| 25 | 12 | 1 | 12 | 4 | 1 | — | 1 | 0.5 | 1 | 2 (Cr) | 340 | 97.5 | 3.0 | 76.8 | 78.8 |

Table 3-continued

| | | | | | | | | | | | | | | | | |
|---|---|---|---|---|---|---|---|---|---|---|---|---|---|---|---|---|
| 26 | 12 | 1 | 12 | 4 | 1 | — | 1 | 0.5 | 1 | 1 (La) | 340 | 96.8 | 3.9 | 77.8 | 80.4 |
| 27 | 12 | 1 | 12 | 4 | 1 | — | 1 | 0.5 | 1 | 4 (Al) | 340 | 97.0 | 3.6 | 77.0 | 79.4 |
| 28 | 12 | 1 | 12 | 4 | 1 | — | 1 | 0.5 | 1 | 2 (Cd) | 340 | 97.2 | 3.4 | 77.5 | 79.7 |
| 29 | 12 | 1 | 12 | 4 | 1 | — | 1 | 0.5 | 1 | 1 (Pb) | 340 | 97.4 | 3.1 | 77.6 | 79.7 |
| 30 | 12 | 1 | 12 | 4 | 1 | — | 1 | 0.5 | 1 | 2 (W) | 340 | 97.4 | 3.0 | 78.4 | 80.5 |
| 31 | 12 | 1 | 12 | 4 | 1 | — | 1 | 0.5 | 1 | 1 (Cu) | 340 | 96.9 | 3.7 | 77.5 | 80.0 |

| | Results of the second-stage oxidation | | | | | |
|---|---|---|---|---|---|---|
| | Reaction | | MAA (based on MAL) | | Conversion of | One-pass yield |
| Example | temperature (°C.) | MAL conversion (%) | One-pass yield (%) | Selectivity (%) | unsaturated hydrocarbons (%) | of MAA (based on i-B) (%) |
| 18 | 335 | 78.3 | 59.3 | 75.7 | 100 | 46.5 |
| 19 | 335 | 77.2 | 58.5 | 75.8 | 100 | 45.7 |
| 20 | 335 | 77.1 | 58.4 | 75.7 | 100 | 45.8 |
| 21 | 335 | 78.0 | 59.4 | 76.2 | 100 | 46.5 |
| 22 | 335 | 77.4 | 58.7 | 75.8 | 100 | 45.1 |
| 23 | 335 | 79.6 | 60.8 | 76.4 | 100 | 46.8 |
| 24 | 335 | 77.0 | 58.1 | 75.5 | 100 | 44.8 |
| 25 | 335 | 78.1 | 59.2 | 75.8 | 100 | 45.5 |
| 26 | 335 | 76.2 | 57.2 | 75.1 | 100 | 44.5 |
| 27 | 335 | 77.2 | 58.9 | 76.3 | 100 | 45.4 |
| 28 | 335 | 77.5 | 59.3 | 76.5 | 100 | 46.0 |
| 29 | 335 | 77.8 | 58.8 | 75.6 | 100 | 45.6 |
| 30 | 335 | 78.4 | 59.7 | 76.1 | 100 | 46.8 |
| 31 | 335 | 77.1 | 58.1 | 75.4 | 100 | 45.0 |

EXAMPLES 32 to 44

Catalysts were prepared in the same way as in Examples 1 and 6 by replacing the X component of the catalysts of Examples 1 and 6 by arsenic or boron, and by replacing the R component of the catalysts by rubidium, cesium or thallium. A continuous first stage-second stage reaction was performed by the same procedure as in Example 1 using these catalysts. The results are shown in Table 4.

results of reactions were examined. As a control, the same test was performed using a catalyst not containing Au and Nd. The results are shown in Table 5.

The results in Table 5 show that the catalysts of this invention containing Au or Nd are suitable for the continuous first stage-second stage method because they give high conversions and selectivity in the first-stage oxidation and extremely reduce the formation of by-product unsaturated hydrocarbons. In contrast, the catalyst not containing the aforesaid ingredients (control) has poor performance in the first-stage oxidation, and gives large amounts of by-product unsaturated hydrocarbons. For this reason, when such a catalyst is used as a first-stage oxidation catalyst in the continuous first stage-second stage method, the lifetime of the second-stage oxidation catalyst is shortened.

Table 4

| | Results of the first-stage oxidation | | | | | | | | | | | | | | | |
|---|---|---|---|---|---|---|---|---|---|---|---|---|---|---|---|---|
| | Catalyst composition (atomic ratio) | | | | | | | | | | | | | Reaction temperature (°C.) | i-B conversion (%) | Proportion of unsaturated hydrocarbons formed (%) | MAL | |
| Example | Mo | Bi | Fe | Co | Ni | Au | Nd | P | As | B | K | Rb | Cs | Tl | | | | One-pass yield (%) | Selectivity (%) |
| 32 | 12 | 1 | 12 | 4 | 1 | 1 | — | — | — | 0.5 | 1 | — | — | — | 340 | 97.5 | 3.5 | 76.6 | 78.6 |
| 33 | 12 | 1 | 12 | 4 | 1 | 1 | — | 0.5 | — | — | — | — | 0.1 | — | 340 | 96.8 | 3.9 | 76.6 | 79.1 |
| 34 | 12 | 1 | 12 | 4 | 1 | 1 | — | 0.5 | — | — | — | 0.75 | — | — | 340 | 97.7 | 3.4 | 76.6 | 78.4 |
| 35 | 12 | 1 | 12 | 4 | 1 | 1 | — | — | 0.5 | — | — | — | — | 0.75 | 340 | 96.9 | 3.7 | 77.0 | 79.5 |
| 36 | 12 | 1 | 12 | 4 | 1 | — | 1 | — | — | — | 1 | — | — | — | 340 | 96.4 | 4.0 | 76.4 | 79.3 |
| 37 | 12 | 1 | 12 | 4 | 1 | — | 1 | — | 0.5 | — | 1 | — | — | — | 340 | 97.0 | 3.6 | 76.4 | 78.8 |
| 38 | 12 | 1 | 12 | 4 | 1 | — | 1 | — | — | 0.5 | 1 | — | — | — | 340 | 97.2 | 3.5 | 76.6 | 78.8 |
| 39 | 12 | 1 | 12 | 4 | 1 | — | 1 | 0.5 | — | — | — | — | 0.1 | — | 340 | 97.0 | 3.3 | 76.6 | 79.0 |
| 40 | 12 | 1 | 12 | 4 | 1 | — | 1 | 0.5 | — | — | — | — | — | 1 | 340 | 96.8 | 3.5 | 75.2 | 77.7 |
| 41 | 12 | 1 | 12 | 4 | 1 | — | 1 | 0.5 | — | — | — | 0.75 | — | — | 340 | 97.1 | 3.5 | 76.2 | 78.5 |
| 42 | 12 | 1 | 12 | 4 | 1 | — | 1 | 0.5 | — | 0.5 | 0.75 | — | — | — | 340 | 97.1 | 3.6 | 75.8 | 78.1 |
| 43 | 12 | 1 | 12 | 4 | 1 | — | 1 | — | 0.5 | — | — | — | — | 0.75 | 340 | 96.7 | 3.6 | 76.0 | 78.6 |
| 44 | 12 | 1 | 12 | 4 | 1 | — | 1 | 0.5 | — | — | 0.5 | 0.5 | — | — | 340 | 96.9 | 3.5 | 76.4 | 78.8 |

EXAMPLES 45 to 48

The continuous first stage-second stage reaction in Examples 1, 6, 7 and 22 was continued for 1000 hours under the same reaction conditions. Changes in the Table 5

| | | | | | | | | | | | Results of the first-stage oxidation | | | |
|---|---|---|---|---|---|---|---|---|---|---|---|---|---|---|---|
| | Catalyst composition (atomic ratio) | | | | | | | | | | The reaction time which passed (hours) | Reaction temperature (°C.) | i-B conversion (%) | Proportion of unsaturated hydrocarbons formed (%) | MAL | |
| Example | Mo | Bi | Fe | Co | Ni | Au | Nd | P | K | Ce | | | | | One-pass yield (%) | Selectivity (%) |
| Control | 12 | 1 | 6 | 4 | 1 | — | — | 0.5 | 1 | — | 0* | 370 | 94.9 | 10.3 | 60.4 | 63.7 |
| | | | | | | | | | | | 1000 | 370 | 94.0 | 11.2 | 60.1 | 63.9 |

Table 5-continued

| | Catalyst composition (atomic ratio) | | | | | | | | | | The reaction time which passed (hours) | Results of the first-stage oxidation | | | | |
|---|---|---|---|---|---|---|---|---|---|---|---|---|---|---|---|---|
| | | | | | | | | | | | | Reaction tempera-ture (°C.) | i-B con-version (%) | Proportion of unsaturated hydrocarbons formed (%) | MAL One-pass yield (%) | Selec-tivity (%) |
| Ex-ample | Mo | Bi | Fe | Co | Ni | Au | Nd | P | K | Ce | | | | | | |
| 45 | 12 | 1 | 12 | 4 | 1 | 1 | — | 0.5 | 1 | — | 0* | 340 | 96.8 | 3.9 | 76.5 | 79.0 |
| | | | | | | | | | | | 1000 | 340 | 96.9 | 3.8 | 76.6 | 79.1 |
| 46 | 12 | 1 | 12 | 4 | 1 | — | 1 | 0.5 | 1 | — | 0* | 340 | 96.7 | 3.9 | 76.3 | 78.9 |
| | | | | | | | | | | | 1000 | 340 | 97.0 | 3.7 | 77.1 | 79.5 |
| 47 | 12 | 1 | 6 | 4 | 1 | — | 1 | 0.5 | 1 | — | 0* | 370 | 96.5 | 4.2 | 75.4 | 78.1 |
| | | | | | | | | | | | 1000 | 370 | 96.5 | 4.2 | 75.0 | 77.7 |
| 48 | 12 | 1 | 12 | 4 | 1 | — | 1 | 0.5 | 1 | 1 | 0* | 340 | 97.1 | 3.4 | 76.8 | 79.1 |
| | | | | | | | | | | | 1000 | 340 | 97.3 | 3.3 | 77.2 | 79.3 |

*The symbol (*) denotes the early stage of reaction.

EXAMPLES 49 to 52

Using the first-stage oxidation catalysts used in Examples 45 to 48, a continuous first stage-second stage reaction was performed in the same way as in Example 1 except that propylene was used as a starting gas instead of isobutylene. The results of the reaction are shown in Table 6.

Table 6

| | Catalyst composition (atomic ratio) | | | | | | | | | | Results of the first-stage oxidation | | | | |
|---|---|---|---|---|---|---|---|---|---|---|---|---|---|---|---|
| Ex-ample | Mo | Bi | Fe | Co | Ni | Au | Nd | P | K | Ce | Reaction tempera-ture (°C.) | Conversion of propylene (%) | Proportion of unsaturated hydrocarbons formed (%) | Acrolein One-pass yield (%) | Selec-tivity (%) |
| 49 | 12 | 1 | 12 | 4 | 1 | 1 | — | 0.5 | 1 | — | 360 | 98.1 | 2.3 | 83.8 | 85.4 |
| 50 | 12 | 1 | 12 | 4 | 1 | — | 1 | 0.5 | 1 | — | 360 | 98.6 | 1.9 | 84.6 | 85.8 |
| 51 | 12 | 1 | 6 | 4 | 1 | — | 1 | 0.5 | 1 | — | 360 | 98.2 | 2.1 | 82.7 | 84.2 |
| 52 | 12 | 1 | 12 | 4 | 1 | — | 1 | 0.5 | 1 | 1 | 360 | 98.7 | 1.8 | 84.9 | 86.0 |

| | Results of the second-stage oxidation | | | | | |
|---|---|---|---|---|---|---|
| Example | Reaction tempera-ture (°C.) | Acrolein con-version (%) | Acrylic Acid (based on acrolein) | | Conversion of unsaturated hydrocarbons (%) | One-pass yield of acrylic acid (based on i-B) (%) |
| | | | One-pass yield (%) | Selectivity (%) | | |
| 49 | 360 | 88.4 | 79.4 | 89.8 | 100 | 66.5 |
| 50 | 360 | 88.9 | 80.0 | 90.0 | 100 | 67.7 |
| 51 | 360 | 88.4 | 79.6 | 90.0 | 100 | 65.8 |
| 52 | 360 | 89.3 | 80.8 | 90.5 | 100 | 68.6 |

What we claim is:

1. A process for preparing unsaturated aldehydes, which comprises oxidizing olefins containing 3 carbon atoms in the straight chain in the vapor phase with molecular oxygen as the oxidizing source in the presence of a catalyst at a temperature of 250° to 700° C., said catalyst having a composition of the following formula:

$Mo_aBi_bFe_cCo_dNi_eQ_fR_gX_hZ_iO_j$ wherein Q is at least one element selected from Au and Nd; R is at least one element selected from K, Rb, Cs and Tl; X is at least one element selected from P, As and B; Z is at least one element selected from Ce, Ti, Te, Zn, Ge, Sn, Cr, Ga, La, In, Al, Cd, Pd, Mn, V, W, Pb, Nb, Ag, Zr, Cu and U; a, b, c, d, e, f, g, h and i respectively represent the numbers of Mo, Bi, Fe, Co, Ni, Q, R, X and Z atoms, and when a is 12, b is 0.1-10, c is 0.5-40, d is 0-12, e is 0-12 with the proviso that the sum of d and e is 0.5-15, f is 0.1-8, g is 0.01-5, h is 0-5, i is 0-12; and j is the number of oxygen atoms which satisfies the atomic valences of the other elements.

2. The process of claim 1 wherein when a is 12, b is 0.5-7, c is 1-35, d is 0-10, e is 0-10 with the proviso that the sum of d and e is 0.5-12, f is 0.1-6, g is 0.01-4, h is 0-4, and i is 0-8.

3. The process of claim 1 wherein when a is 12, b is 0.5-7, c is 8-30, d is 0-10, e is 0-10 with the proviso that the sum of d and e is 0.5-12, f is 0.1-4, g is 0.01-3, h is 0-3, and i is 0-8.

4. The process of claim 1 wherein R is K.
5. The process of claim 1 wherein R is Rb.
6. The process of claim 1 wherein R is Cs.
7. The process of claim 1 wherein R is Tl.
8. The process of claim 1 wherein Q is Au.
9. The catalyst of claim 1 wherein Q is Nd.
10. The process of claim 1 wherein air is used as a source of oxygen.
11. The process of claim 1 wherein the reaction is carried out in the presence of an inert gas.
12. A process according to claim 1, wherein the temperature of reaction is 250°-550° C.

* * * * *